: US005808071A

United States Patent [19]
Watson

[11] Patent Number: 5,808,071
[45] Date of Patent: Sep. 15, 1998

[54] PICTET-SPENGLER REACTION FOR THE SYNTHESIS OF TETRAHYDROISOQUINOLINES AND RELATED HETEROCYCLIC COMPOUNDS

[75] Inventor: Timothy James-Norman Watson, Centerville, Ohio

[73] Assignee: Hoechst Marion Roussell, Inc., Cincinnati, Ohio

[21] Appl. No.: 893,303

[22] Filed: Jul. 15, 1997

Related U.S. Application Data

[60] Provisional application No. 60/064,852 Sep. 27, 1996.
[51] Int. Cl.[6] .................... C07D 217/02; C07D 221/20; C07D 209/44; C07D 209/70
[52] U.S. Cl. ............................ 546/18; 540/604; 546/141; 548/411; 548/482
[58] Field of Search ....................... 546/141, 18; 548/482

[56] References Cited

U.S. PATENT DOCUMENTS 5,292,746   3/1994   Carr et al. ................................ 514/278

OTHER PUBLICATIONS

Lukanov et. al., Synthesis, (2) pp. 204–206, Feb. 1987.
Ito, et al., Syntheses of 1,2,3,4–Tetrahydroisoquinolines from N–Sulfonyl–phenethylamines and Aldehydes, Chem. Pharm. Bull., 25(7):1732–1739, (1977).
Blicke, F.F., The Mannich Reaction,Org. Reactions, 1, Chap. 10 pp. 303–341, (1942).
Chen, H.G., et al., Pictet–Spengler Cyclization of 3,3–Diphenylalanine (DIP) (III), Synthesis of Optically Pure 1,2,3,4–Tetrahydro–4–Phenyl–3–Isoquinolinecarboxylic acids, novel α–Amino Acids for Peptides of Biological Interest, Synthetic Comm., 2591), 49–56 (1995)
Saito, N., et al., A Facile Synthesis of 1,2,3,4–Tetrahydroisoquinolines through Cyclization of O,N–Acetals.II. these os o Isoquinolinequinone Antibiotics Chem. Pharm. Bull., 37(6) 1493–1499 (1989).
Whaley, W.M., et al., The Pictet–Spengler Synthesis of tetrahydroisoquinolines and Related Compounds, Organic Reactions, Chap. 3, pp. 151–159 (1951).
Remers, W.A., et al., Synthesis of Indoles from 4–Oxo–4, 5,6,7–tetrahydoindoles. II. Introduction of Substituents into the 4 and 5 Positions J. Org. Chem. 36(9) 1232–1240 (1971).
Cox E. D., et al., The Pictet–Spengler Condensation: A New Direction for an Old Reaction, Chem. Rev. 95, 1797–1842 (1995).

*Primary Examiner*—Bernard Dentz
*Attorney, Agent, or Firm*—Balaram Gupta; William R. Boudreaux

[57] ABSTRACT

A commercial scale process for the production of tetrahydroisoquinolines and related heterocyclics by reaction, in mildly acidic conditions, of aryl N-sulfonylethylamines in the presence of a suitable Lewis acid, and a compound capable of in situ generation of formaldehyde. The process is further characterized by formaldehyde being generated by the reaction of the Lewis acid upon the formaldehyde generating agent, instead of being present as an initial reactant. The process further avoids the presence of initial water which destroys the Lewis acid before it can act upon the formaldehyde generating agent.

34 Claims, No Drawings

PICTET-SPENGLER REACTION FOR THE SYNTHESIS OF TETRAHYDROISOQUINOLINES AND RELATED HETEROCYCLIC COMPOUNDS

This application claims the benefit of Provisional application Ser. No. 60/064,852, filed Sep. 27, 1996.

BACKGROUND OF THE INVENTION

The present application relates to a novel synthesis for certain tetrahydroisoquinolines which are useful intermediates in the preparation of certain cyclic nitrones which have multiple pharmaceutical utility, including for example, the prevention of oxidative tissue damage from oxygen based free radicals and the inhibition of interleuken-1. The utility of these cyclic nitrones and their advantages are better described in U.S. Pat. No. 5,292,746.

The Pictet-Spengler reaction is a condensation of a β-arylethylamine with a carbonyl compound to yield a tetrahydroisoquinoline, and is a specific example of the more general Mannich reaction. It has been generally accepted that the reactivity of the aromatic nucleus of the arylethylamine as well as the carbonyl reactant are significant to the success of the reaction. Whaley, W. M. & Govindachari, T. R., Organic Reactions 6:151–190 (1951), the disclosure of which is herein incorporated by reference. Formaldehyde is routinely employed, as it is cheap, reactive and effective. More importantly, Whaley and Govindachari have noted that the activation of the aromatic ring, by some form of electrophilic substitution para to point of ring closure was necessary before the reaction will proceed.

The production of tetrahydroisoquinolines by way of Pictet-Spengler condensation of unsubstituted aryl N-sulfonylethylamines was described by K. Ito and H. Tanaka in Chem. Pharm Bull. 25(7), 1732–1739 (1977), the disclosure of which is herein incorporated by reference. The process conditions described the reaction in chloroform between N-sulfonatedphenethylamines with aqueous formaldehyde in the presence of $BF_3$-etherate. Because the formaldehyde was in an aqueous solution, and water is destructive of the $BF_3$-etherate, the $BF_3$-etherate must be used in substantial molar excess. This procedure is viable on a small laboratory scale, but is too inefficient and expensive to be applicable to a commercial scale synthesis.

SUMMARY OF THE INVENTION

Applicants have created a process for the commercial scale production of tetrahydroisoquinolines and related heterocyclics by reaction, in mildly acidic conditions, of aryl N-sulfonylethylamines in the presence of a suitable Lewis acid, and a compound capable of in situ generation of formaldehyde. Applicants invention is an improvement upon the Ito and Tanaka process, in that water is not present as an initial reactant (The formaldehyde used was a 37% aqueous solution). Applicant's process is also characterized by formaldehyde being generated by the reaction of the Lewis acid (boron trifluoroetherate) upon the $CH_2O$ generating agent, instead of being present as an initial reactant. The in situ generation of formaldehyde is advantageous because presently formaldehyde reagent is only available as a 37% aqueous solution, requiring a substantial molar excess of the Lewis acid to compensate for that which is deactivated by water.

The invention describes a process for creating a compound of the formula:

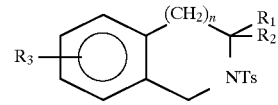

wherein $R_1$ and $R_2$ are each independently $C_{1-3}$ alkyl or $R_1$ and $R_2$ together form $C_{2-7}$ alkylene, n is an integer from 0–2, $R_3$ is hydrogen, halogen, $C_{1-4}$ alkyl, $C_{1-4}$ alkoxy, $-CF_3$, $-OCF_3$ and $-OH$, and Ts is para-toluenesulfonyl.

by reacting under alkaline conditions a compound of the formula:

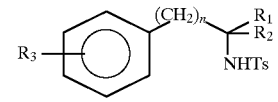

with a suitable Lewis acid in a formaldehyde generating solvent.

DETAILED DESCRIPTION OF THE INVENTION

As used herein, the term "suitable Lewis acid" means a strongly electrophilic compound capable of combining with another molecule by forming at least one covalent bond with two electrons from the second molecule. For example, borontrifluoro etherate ($BF_3 \cdot OEt_2$), aluminum chloride ($AlCl_3$), zinc chloride ($ZnCl_2$), magnesium bromide ($MgCl_2$), ferric chloride ($FeCl_3$). The preferred Lewis acid is borontrifluoro etherate.

As used herein, the term "formaldehyde generating solvent" means dimethoxy methane, paraformaldehyde, diethoxyethane, bis(methylthio)methane ($CH_2(SCH_3)_2$). The preferred formaldehyde generating agent is dimethoxy methane.

As used herein, the term "$C_{1-3}$ alkyl" means methyl, ethyl, n-propyl, isopropyl.

As used herein, the term "$C_{2-7}$ alkylene" means a straight chain alkyl bridge of two valences, such that the same atom does not have both valences. For example, ethylene, n-propylene, n-butylene, n-pentylene, n-hexylene, n-heptylene.

As used herein, the term "halogen" means fluoro, chloro, bromo, iodo.

As used herein, the term "$C_{1-4}$ alkyl" means a straight or branched chain alkyl from one to four carbon atoms. For example, methyl, ethyl, n-propyl, isopropyl, n-butyl, s-butyl, t-butyl.

As used herein, the term "$C_{1-4}$ alkoxy" means a straight or branched alkoxy group from one to four carbon atoms. For example, methoxy, ethoxy, n-propoxy, isopropoxy, n-butoxy, s-butoxy, t-butoxy.

The present invention is a useful part of a multi-step synthesis for the creation of certain cyclic nitrones useful in the prevention of oxidative tissue damage and which are described in U.S. Pat. No. 5,292,746. More particularly, this synthesis may be carried out as follows:

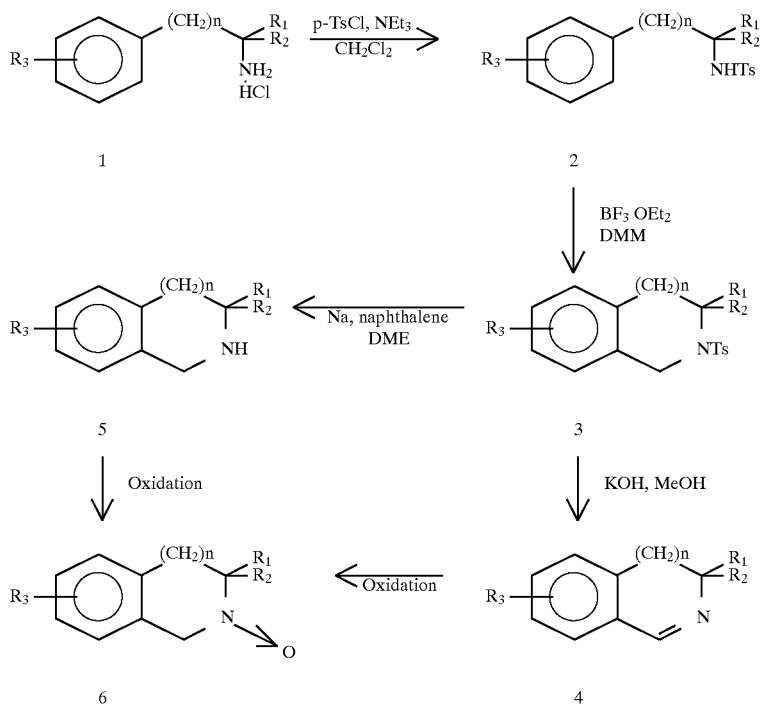

In the above scheme, the tosylated amine [2] may be prepared, as indicated by Ito and Tanaka, in the presence of three molar equivalents of triethylamine (NEt$_3$). The tosylated amine may then be converted into the tetrahydroisoquinoline or related heterocyclic [3] as described by the present invention. This compound, as is known, can then be subjected to alkaline conditions to afford the dihydro analog [4], Remers, W. A. et al, *J. Org. Chem.* 36, 1232–1240 (1971) or treated with sodium naphthalenide in DME to give the unprotected cyclic amine [5] Heathcock et al., *J. Org. Chem.* 54:7, 1548–1562 (1989). Compound [4] or [5] may then be oxidized into the nitrone [6], for example, by application of sodium tungstate (NaWO$_4$, as is described in "Synthesis and Radical Scavenging Activity of 3,3-Dialkyl-3,4-Dihydro-Isoquinoline-2-Oxides," Bioorganic & Medicinal Chemistry Letters, (in press), Berotas, R. C. et al.

The following examples are given to illustrate in further detail the practice of the invention, but should not be construed as limiting it in any way.

EXAMPLE 1

To a nitrogen-blanketed solution of 1,1-dimethyl-2-phenyl-ethylamine (3.56 g, 0.019 mol), methylene chloride (CH$_2$Cl$_2$, 20 mL) and triethylamine (Et$_3$N, 8.01 mL, 0.058 mol) was added para-toluenesulfonyl chloride (TsCl, 4.39 g, 0.023 mol). The mixture was stirred at room temperature for 12 hours while monitoring by gas chromatography. The reaction mixture was partitioned between methylene chloride (100 mL) and water (100 mL) and the organic layer was separated and dried over sodium sulfate. The drying agent was filtered off and the filtrate was concentrated to give 5.73 g of N-toluenesulfonyl-1,1-dimethyl-2-phenyl-ethylamine (yield=99%).

IR (Kbr, cm-1) 3443, 3283, 1311, 1097; $^1$H-NMR (300 Mhz, CDCl$_3$) δ7.72 (m, 2H), 7.21–7.35 (m, 7H), 4.50 (bs, 1H), 2.83 (s, 2H), 2.40 (s, 3H), 1.18 (s, 6H); $^{13}$C-NMR (75 Mhz, CDCl$_3$) ppm 142.8, 140.6, 136.6, 130.8, 129.4, 128.2, 126.9, 126.7, 56.9, 49.0, 27.4, 21.5; MS m/z (M$^+$) calc'd 303.4, observed 304.

Analysis calc'd for C$_{17}$H$_{21}$NO$_2$S: C, 67.30; H, 6.98; N, 4.62. Found: C, 67.23; H, 6.90; N, 4.55.

EXAMPLE 2

To a nitrogen-blanketed mixture of N-toluenesulfonyl-1,1-dimethyl-2-phenyl-ethylamine (8.30 g, 0.027 mol.) in dimethoxymethane (50 mL) was added boron trifluororo etherate (BF$_3$·OEt$_2$, 9.9 mL, 0.081 mol.). The mixture was stirred at room temperature for 12 hours while monitoring by gas chromatography. The reaction mixture was partitioned between ethyl acetate (100 mL) and water (100 mL), separated, and the organic layer is washed with saturated sodium bicarbonate (2×100 mL) and dried over sodium sulfate (Na$_2$SO$_4$). The drying agent was filtered off and the filtrate was concentrated at 40°/50 torr to give 8.55 g of N-toluenesulfonyl-3,3-dimethyl-1,2,3,4-tetrahydroisoquinoline (yield=99%).

IR (KBr, cm$^{-1}$) 3441, 2984, 1338, 1159; $^1$H-NMR (300 Mhz, CDCl$_3$) δ7.65 (m, 2H), 7.05–7.25 (m, 7H), 4.59 (s, 2H), 2.39 (s, 3H), 1.40 (s, 6H); $^{13}$C-NMR (75 Mhz, CDCl$_3$) ppm 142.7, 139.7, 134.5, 133.6, 129.4, 128.1, 127.2, 126.9, 126.4, 125.4, 58.1, 46.9, 44.9, 27.7, 21.4; MS m/z(M$^+$) calc'd 315.4, observed 315.

Anal. calc'd for C$_{18}$H$_{21}$NO$_2$S: C, 68.54; H, 6.71; N, 4.44. Found: C, 68.14; H, 6.70; N, 4.37.

EXAMPLE 3

To a nitrogen-blanketed mixture of potassium hydroxide (KOH, 30 g) and methanol (CH$_3$OH, 60 mL) was added of N-toluenesulfonyl-3,3-dimethyl-1,2,3,4-tetrahydroisoquinoline (4.0 g, 0.013 mol.). The reaction mixture was heated at reflux for 17 hours and the reaction was followed by gas chromatography. The reaction mixture was cooled to ambient temperature, quenched with water (100 mL) and 10% HCl was slowly added until pH=7 was obtained. The aqueous mixture was extracted with methylene chloride (3×100 mL) and the organic layers were combined and stirred with charcoal and sodium sulfate ($Na_2SO_4$). The solution was filtered through celite and the filtrate was concentrated (25°/150 torr) to give 3,3-dimethyl-3,4-dihydroisoquinoline (1.79 g, yield=90%).

IR (neat, $cm^{-1}$) 3389, 2966, 1628; $^1$H-NMR (300 Mhz, $CDCl_3$) δ8.23 (s, 1H), 7.40–7.15 (m, 4H), 2.72 (s, 2H), 1.25 (s, 6H); $^{13}$C-NMR (75 Mhz, $CDCl_3$) ppm 157.4, 135.6, 131.0, 128.0, 127.5, 127.0, 126.9, 54.7, 37.9, 28.0; MS m/z($M^+$) calc'd 159.23, observed 159.

EXAMPLE 4

To a stirred solution of naphthalene (5.8 g, 0.045 mol) in dimethoxyethane (50 mL) was added sodium metal (1.09 g, 0.039 mol.). The mixture was allowed to stir for four (4) hours until a dark green color persisted. To this was added of N-toluenesulfonyl-3,3-dimethyl-1,2,3,4-tetrahydroisoquinoline (5.0 g, 0.016 mol.) in 20 mL of dimethoxymethane. The reaction was monitored by gas chromatography. When the reaction was complete (≈2 hours), the mixture was quenched with saturated sodium chloride (70 mL). The mixture was partitioned between ethyl acetate (250 mL) and 10% HCL (250 mL) and the organic layer was discarded. 10% Sodium hydroxide was added to the aqueous layer until a pH=7 was obtained. The aqueous layer was further extracted over methylene chloride (2×100 mL), dried over magnesium sulfate, filtered and concentrated (25° C./150 torr) to produce 2.2 g (86%) of 3,3-dimethyl-1,2,3,4-tetrahydroisoquinoline.

IR (neat, $cm^{-1}$) 3043, 2897, 744; $^1$H-NMR (300 Mhz, $CDCl_3$) δ7.14–7.00 (m, 4H), 4.02 (s, 2H), 2.61 (s, 2H), 1.58 (bs, 1H), 1.19 (s, 6H); $^{13}$C-NMR (75 Mhz, $CDCl_3$) 134.5, 134.4, 129.5, 125.9, 125.6, 125.5, 48.6, 44.3, 41.5, 27.7; MS m/z ($M^+$) calc'd 161.24, observed 161.

I claim:

1. A process for creating a compound of the formula:

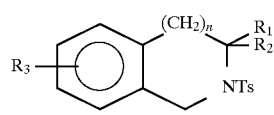

wherein $R_1$ and $R_2$ are each independently $C_{1-3}$ alkyl or $R_1$ and $R_2$ together form $C_{2-7}$ alkylene, n is an integer from 0–2, $R_3$ is hydrogen, halogen, $C_{1-4}$ alkyl, $C_{1-4}$ alkoxy, $—CF_3$, $—OCF_3$ and $—OH$, and Ts is para-toluenesulfonyl.

by reacting under alkaline conditions a compound of the formula:

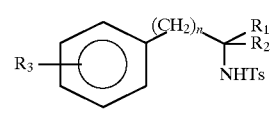

with a suitable Lewis acid in a formaldehyde generating solvent.

2. The process of claim 1 wherein the Lewis acid is selected from the group consisting of boron trifluoroetherate ($BF_3·OEt_2$), aluminum chloride, zinc chloride, magnesium bromide, ferric chloride ($FeCl_3$).

3. The process of claim 2 wherein the Lewis acid is boron trifluoroetherate.

4. The process of claim 1 wherein the formaldehyde generating solvent is selected from the group consisting of dimethoxymethane, paraformaldehyde, diethoxyethane, bis(methylthio)methane.

5. The process of claim 4 wherein the formaldehyde generating solvent is dimethoxymethane.

6. The process of claim 1 wherein $R_1$ and $R_2$ are each $C_{1-3}$ alkyl.

7. The process of claim 1 wherein $R_3$ is hydrogen.

8. The process of claim 1 wherein n is 1.

9. The process of claim 1 wherein n is 0.

10. The process of claim 1 wherein $R_3$ is hydrogen, n is 1 and $R_1$ and $R_2$ are each methyl.

11. The process of claim 1 wherein $R_3$ is hydrogen, n is 1, and $R_1$ and $R_2$ combined are $—(CH_2)_5—$ or $—(CH_2)_4—$.

12. The process of claim 1 wherein the compound created is:

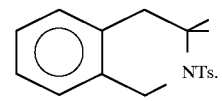

13. The process of claim 1 wherein the compound created is:

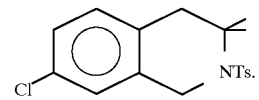

14. The process of claim 1 wherein the compound created is:

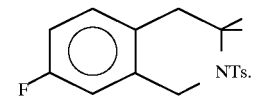

15. The process of claim 1 wherein the compound created is:

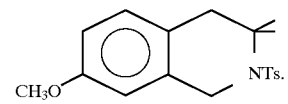

16. The process of claim 1 wherein the compound created is:

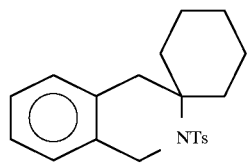

17. The process of claim 1 wherein the compound created is:

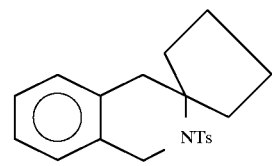

18. The process of claim 1 wherein the compound created is:

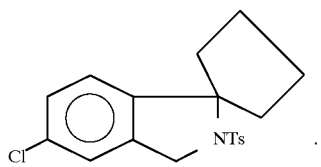

19. The process of claim 1 wherein the compound created is:

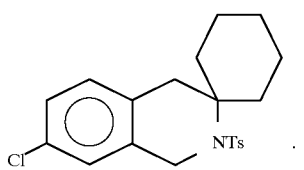

20. The process of claim 1 wherein the compound created is:

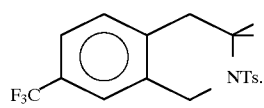

21. The process of claim 1 wherein the compound created is:

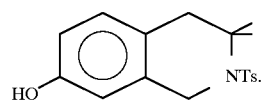

22. The process of claim 1 wherein the compound created is:

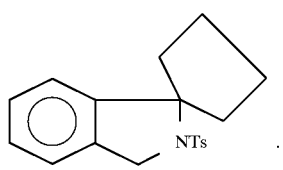

23. The process of claim 1 wherein the compound created is:

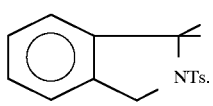

24. The process of claim 1 wherein the compound created is:

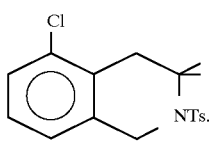

25. The process of claim 1 wherein the compound created is:

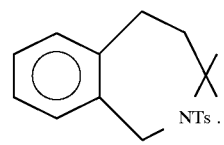

26. The process of claim 1 wherein the compound created is:

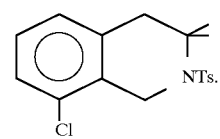

27. The process of claim 1 wherein the compound created is:

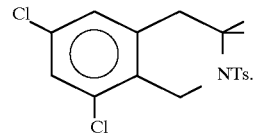

28. The process of claim 1 wherein the compound created is:

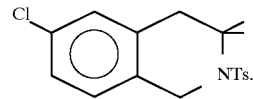

29. The process of claim 1 wherein the compound created is:

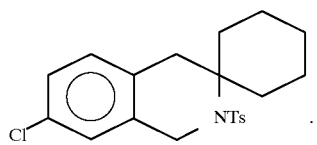

30. The process of claim 1 wherein the compound created is:

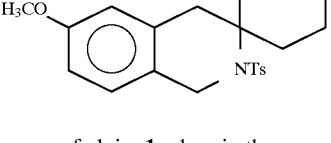

31. The process of claim 1 wherein the compound created is:

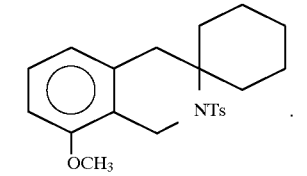

32. The process of claim 1 wherein the compound created is:

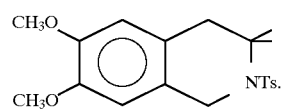
33. The process of claim 1 wherein the compound created is:
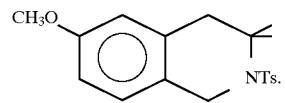
34. The process of claim 1 wherein the compound created is:
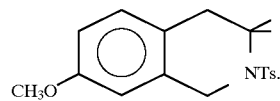
* * * * *